United States Patent [19]

Fabinski et al.

[11] Patent Number: 5,003,175

[45] Date of Patent: Mar. 26, 1991

[54] CALIBRATION OF NONDISPERSIVE INFRARED PHOTOMETER

[75] Inventors: Walter Fabinski, Kriftel; Georg Taubitz, Oberursel; Joachim H. von Wolfframsdorff, Seeheim-Jugenheim, all of Fed. Rep. of Germany

[73] Assignee: Hartmann & Braun AG, Frankfurt, Fed. Rep. of Germany

[21] Appl. No.: 359,510

[22] Filed: Jun. 1, 1989

[30] Foreign Application Priority Data

Jun. 1, 1988 [DE] Fed. Rep. of Germany ....... 3818598

[51] Int. Cl.$^5$ .......................................... G01N 21/61
[52] U.S. Cl. .................................. 250/345; 250/343; 250/252.1; 73/1 G
[58] Field of Search ................ 250/343, 345, 252.1 R

[56] References Cited

U.S. PATENT DOCUMENTS

| 2,674,696 | 4/1954 | Smith et al. | 250/345 |
| 3,072,787 | 1/1963 | Moyat | 250/343 |
| 3,193,676 | 7/1965 | Smart | 250/345 |
| 3,560,738 | 2/1971 | Strange | 250/343 |
| 3,805,074 | 4/1974 | McCormack | 250/354.1 |
| 4,204,768 | 5/1980 | N'Guyen | 250/243 |
| 4,673,812 | 6/1987 | Yoneda | 250/252.1 |
| 4,794,255 | 12/1988 | Miyatake et al. | 250/343 |

FOREIGN PATENT DOCUMENTS 3522949 1/1987 Fed. Rep. of Germany .
2826522 4/1988 Fed. Rep. of Germany .

Primary Examiner—Constantine Hannaher
Assistant Examiner—Edward J. Glick
Attorney, Agent, or Firm—Ralf H. Siegemund

[57] ABSTRACT

The photometer is calibrated by using a permanently built-in installation of four, similarly configured chambers in a good heat conducting carrier which is slidably interposed between sample and reference chambers on one hand and the detection structure on the other hand. One pair of these chambers is placed in the paths during measurement and is filled with inert gas, the other pair has one chamber filled with calibration gas, the other one with inert gas. All chambers are closed with similar windows.

5 Claims, 2 Drawing Sheets

CALIBRATION OF NONDISPERSIVE INFRARED PHOTOMETER

BACKGROUND OF THE INVENTION

The present invention relates to calibrating a nondispersive infrared photometer, and more particularly the invention relates to a calibrating device for use in conjunction with a nondispersive infrared photometer; such a photometer includes an infrared radiation source and a radiation modulator; and a twin or double sample chamber with symmetrically configured measuring and reference ray paths for purposes of selective absorption of infrared radiation passing through. The photometer further includes a receiver and a filter device for the infrared radiation to provide for certain selectivity in the detection process. This kind of a photometer is to be calibrated by use of calibration chambers which contain particular gases to be placed into the radiation path mentioned above, whereby specifically for purposes of measuring different chambers each being filled with an inert gas are placed in the respective optical path, while during calibration operation an alternate chamber pair is shifted into the radiation path wherein in one chamber a calibration gas is provided while the other one, a reference chamber, is provided with an inert gas.

Within the NDIR photometers of the type to which the invention refers and pertains broadly, a radiation source is used which is basically a thermal radiator. The receiver on the other hand is usually a gas filled absorption chamber or a solid state detector. The absorption path is provided, in the case of extractively operating photometers, in accordance with the measuring principles outlined above. The absorption path is constructed to include twin sample chamber as stated. NDIR photometers of the type to which the invention pertains are by their very nature subject to certain temporal drift, aging etc. The need exists to recalibrate them from time to time.

Recalibrating was carried out in the past in accordance with one kind of state of the art teaching, by using the measuring sample chamber and reference sample chamber of the equipment in the normal course of events but charging it with test gases of known properties. These test gases of course have to be certain and predetermined as to their properties and are usually maintained in metal bottles, flasks or the like which are usually quite heavy. This simple fact renders calibration, particularly recalibration in the field, quite expensive and cumbersome.

German patent application No. 35 22 949 suggests a calibrating chamber which includes a test gas that is sealed therein and from time to time this replacement calibrating chamber is just put into the equipment for test purposes. Peculiarly enough this kind of equipment has not found acceptance, at least it is not generally accepted in NDIR meters. It is believed that the reason for this lack in success results from the fact that the photometers use thermal radiation sources and are thus very sensitive against thermal and optical changes based on thermal changes and vice versa. This is particularly true in the case of a two beam photometer of the type referred to above having a measuring beam path and a reference beam path and wherein a differential signal is produced from signals attributed respectively to the detected measuring beam and to the detected reference beam. Putting a calibrating sample chamber system into the radiation path was found to interfere with the equilibrium of the photometer as a whole owing to the different optical and thermal effect measuring and reference beams undergo. Hence, the resulting measuring signal is in fact distorted during the calibration procedure which of course defeats its purpose. In addition radiation is attenuated owing to a different number of optically effective surfaces of the calibration equipment on one hand and the regular equipment on the other hand.

German patent No. 28 26 522 describes a calibration device wherein a single calibration chamber is shifted into the measuring path or pivoted into the path, while the reference path remains as is. Hence, the problem of optical and thermal symmetry and coupling are not subject to the calibration procedure nor are losses through the gaps or the like taken into consideration. These gaps do produce certain losses and thereby reduce the sensitivity of the equipment. Penetration of air containing $CO_2$, for example from the environment, will definitely interfere with $CO_2$ measurement through uncontrolled preabsorption. Other gases even of unknown consistency that may be happening in the air will compound the problem.

DESCRIPTION OF THE INVENTION

It is an object of the present invention to provide a new and improved calibration method and equipment which is not subject to the drawbacks outlined above.

It is a particular object of the present invention to provide a calibration device for a nondispersive infrared photometer which includes an infrared radiation source, a modulation device, a twin measuring and sample chamber with symmetrically configured measuring and reference path; and further including a receiver and a filter device for providing certain selectivity.

It is another object of the present invention to provide a new and improved calibration device which includes reference chambers with sealed in gases and to be placed from time to time into the meter to be calibrated whereby particularly one sealed chamber is filled with calibration gas and the other one with an inert gas.

In accordance with the preferred embodiment of the present invention, it is suggested to provide the calibration chambers on and in a carrier which is a very good heat conductor and is for example made of copper or a material having a comparable thermal conductivity. These chambers are provided in pairs of similar configuration as far as overall geometry is concerned, they preferably have a semicircular boundary so that the chambers of a pair complement each other geometrically to form a circle. The chambers are sealed with windows permeable to infrared radiation whereby particular care is taken of providing as many optical surfaces in the calibration chamber assembly as are found in the regular measuring operation. One pair of chambers is filled with (optically) inert gas such as nitrogen, the other (calibration) pair has one chamber filled with inert gas preferably the same one as before, while the other one is filled with calibration/measuring gas.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
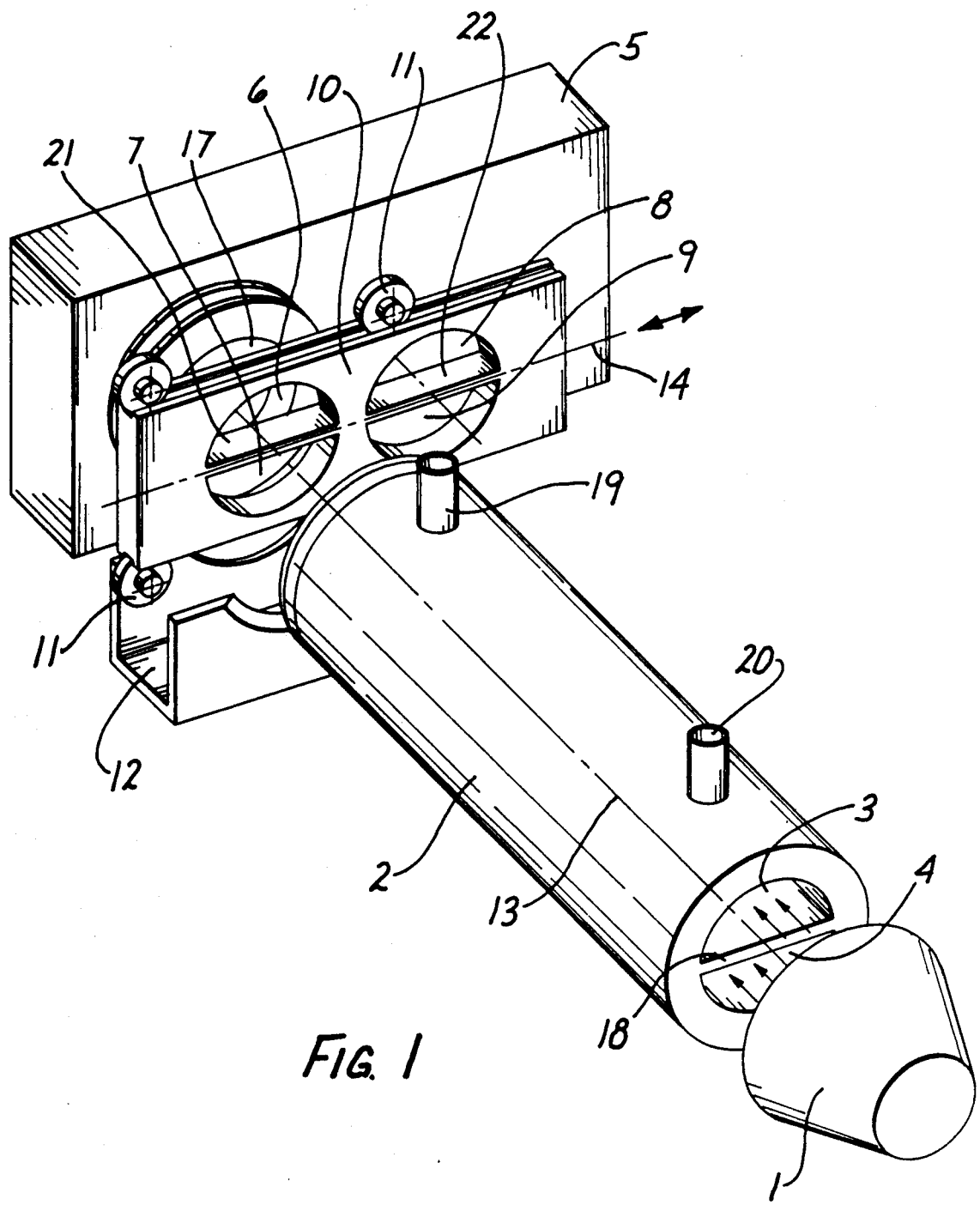
FIG. 1 is a perspective and exploded view from the top, showing calibration equipment for a NDIR photometer in accordance with the preferred embodiment of the present invention for practicing the best mode thereof.

Proceeding now to the detailed description of the drawings, the NDIR meter to be calibrated and recalibrated from time to time includes broadly a source of radiation 1 for generating infrared radiation. A beam modulator (chopper wheel) may be placed in front of this source and the exit window of this radiation source is connected to a twin sample chamber 2 of overall tubular configuration, chamber 2 is provided in a symmetrical arrangement that includes a measuring chamber 3 and a reference chamber 4. The two chambers 3 and 4 have a common entrance window 17. The two chambers 3 and 4 are separated from each other by a transverse wall 18 which establishes of course a plane of symmetry among chambers 3 and 4 and includes the axis of this tube while extending otherwise in a diametrical relationship. The two chambers 3 and 4 have thus semicircular cross section of similar dimensions. Reference numerals 19 and 20 refer to special inlet stubs which provide the measuring chamber 3 with inert gas during the calibration procedure.

Figure 2:
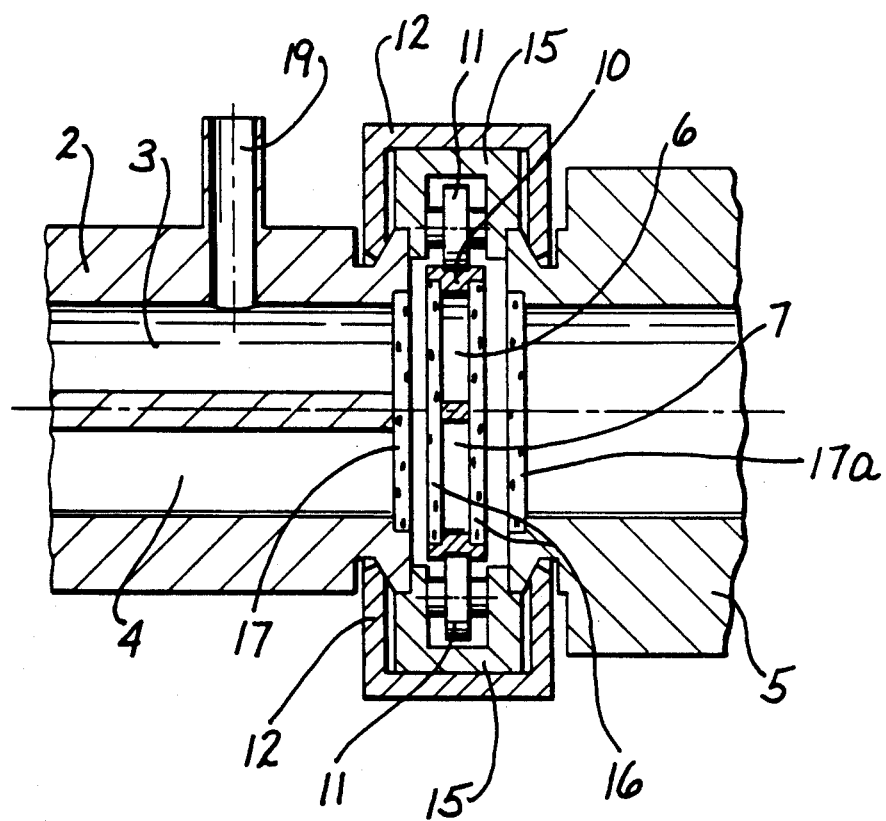
FIG. 2 shows a cross section through a portion as indicated by II—II in FIG. 1.

Reference numeral 10 refers to a plate of a calibration device which includes the plate 10 as a common carrier and is made of copper or the like. Four basically similar sample chambers 6, 7, 8, 9 are inserted and included in plate 10. They are arranged in pairs, as can be seen in FIG. 1, and are each of semicircular configuration; the two chambers 6 and 7 complete a circle but are separated by a diametrically extending bar 21. The same is true with regard to chambers 8 and 9, and a separation bar 22 separates them. These individual chambers 8 and 9 are, as far as cross section is concerned, respectively similar to the chambers 3 and 4. Of course the latter chambers are longer but the cross section i.e. the configuration in a plane transverse to the direction of radiation passing through is the same for all these chambers except that the cross section of chambers 6 and 9 is a little larger than the cross section of sample chambers 3 and 4. The sample chambers are closed through windows such as 16 (see FIG. 2) and these windows are of course transmissive to infrared radiation. These windows are again the same for the normal measuring and sample chamber 3 and 4.

It is now an important feature of the invention that one pair of these chambers, e.g. the chambers 6 and 7, are normally included in the equipment. They are, so to speak, part of the permanent installation for regular measuring operations and in a noninterfering fashion. They are, therefore, optically respectively in series with the measuring and reference chambers. In other words chamber 6 is normally optically in series with chamber 3 and chamber 7 is normally optically in series with chamber 4. Chambers 6 and 7 are both filled with an inert gas which is known not to interfere with the infrared radiation, at least as far as the measuring range is concerned. It is unimportant whether or not these two chambers 6 and 7 are interconnected as far as gas is concerned. Essential is that they provide optically a kind of reference system that is permanently installed in an exchangeable fashion. As far as the measuring procedure is concerned they are always in the radiation paths during normal operation and measuring operation of the equipment.

Now, the second pair of calibration chambers 8 and 9 is exactly configured as the pair 6 and 7 including the optical surfaces offered, or which they are capable of offering. Of course normally these chambers 8 and 9 are in a position that is laterally offset from the measuring path, and chambers 8 and 9 thus do not participate in the normal operation. One of the chambers now is again filled with inert gas while the other one is filled with whatever calibration gas one deems desirable. A calibration gas is for instance a gas of the kind that is to be detected.

The calibration carrier 10 is slidably mounted in the equipment; the carrier 10 is particularly mounted in a particular position relation to the detection system 5 as will be described. The detection system 5 of the photometer is of conventional design and does not play any part in the invention, except of course that measuring and detection operations are used also for calibration purposes, but the type or kind of measurement, detection and reading that is carried out by the detector equipment used is immaterial for the specific purpose of the invention, namely on-the-spot recalibration. Clamps 12 hold detector 5 and plate 10 together which is a very important feature in that it makes sure that the detector 5 is and remains in good heat conductive relationship with plate 10 irrespective of the particular shifting position of that plate. Detector 5 has an entrance window 17a.

The front end of this detector system 5 next to window 17a carries a plurality of guide rollers 11 by means of which the plate 10 or carrier of the calibration device can be shifted with ease. The path of shifting extends of course exactly transverse to the optical axis 13 of the measuring equipment. Reference numeral 14 refers to an axis along which in a symmetrical fashion, the calibration device and particularly the plate 10, is shifted. In the example shown in FIG. 1 of course axis 14 intersects axis 13, and the axis 14 runs right through the separating bars 21 and 22. In addition the axis 14 of movement is situated in the interface between the twin measuring chamber 2 on one hand and the detector system on the other hand.

The carrier 10 is positioned and can be shifted so that either the pair of chambers 6 and 7 or the pair of chambers 8 and 9 is placed in the measuring and reference beam paths. Specifically, and during the transition, there will always be equally dimensional portions of chambers in the two beam path. Hence, there is always simultaneous modification in the two beam paths so that any abrupt change is avoided, as that may affect the relationship between these two paths and in any detection, in particular in the differential mode detection or the like. As stated, the apertures of the chambers 6–9 are for practical purpose a little larger than the apertures of the measuring and reference chambers 3 and 4 in order to avoid positioning errors as they may result from mechanical tolerances or the like that could in cases lead to certain radiation and throttling.

It can readily be seen that the arrangement as shown makes sure that all radiation to the extent it is nor interfered with or modified by any particular gas filling, will be affected in the same way during measuring and during calibration operation. The calibration particularly affects measuring and reference beams equally so that there is compatible behaviour in the signal compensation. In order to reduce any thermal influence on the measureing results it is noted that the carrier 10 of the calibration device is made of a very good heat conductive material such as copper or the like. The two bars 21 and 22 are quite thin so that no matter what the ambient situation is, there is at best only a very minor temperature gradient in between the chambers of each pair. Thermal coupling between adjacent chambers moreover is supported by the fact that the elements which hold and guide the calibration device 10 include clamps 12 and a holding device 15 and that also provides for thermal compensation at the same time around the carrier of the device 10. Through tight geometric coupling between the twin sampling chambers (3,4) of tube 2 on one hand and the detector chamber 5 on the other hand by means of the two clamps 12 gaps in the radiation path are avoided. As was stated above such gaps would produce radiation losses and reduce the sensitivity of the equipment.

It can thus be seen that there is a completely symmetrical configuration wherein measuring and reference branches of the photometer are subjected to radiation in similar fashion under avoidance of measuring distortion and signal and result falsification. The construction is such that positioning errors are avoided and the arrangement provides for basically a thermally balanced system. Any local transverse temperature gradients are avoided or at least made very minimal and can be kept from reducing the sensitivity of the meter.

The temperature of measuring gas and any pressure variations are of course compensated in a manner known per se through temperature and pressure compensation which is included in the electrical signal processing and evaluating part. These aspects are conventional are not claimed and do not require elaboration.

The calibration device by means of a gas filled slidable multiple chamber system as outlined above, and as has been described with reference to plate 10 permits, owing to its symmetry, a very rapid and exact calibration. The recalibration can be carried out frequently; one just has to shift this plate 10 back and forth. The calibration process moreover does not interfere with the optical and thermal equilibrium or balance of and in the meter so that undesirable side effects on that account are avoided.

Owing to the symmetrical configuration and the relative small size and the good thermal coupling in the interface between measuring and detection system sample system, the measuring and reference parts of the photometer are configured such that any modifications, variations, adjustments and so forth will always affect a complete system in the sense that whether there is calibration or measurement or a transition from one to each other, the relationships are maintained particularly in regard to optical end and/or thermal variations. Here then actually the compactness of the design, the interpositioning of a flat carrier 10 between the detection system 5 on one hand and the sample system 2 on the other hand is highly beneficial with regard to reducing parasitic side effects.

Any position error as far as the tube 2 is concerned has very little effect because it is inherently taken in consideration on calibration. This ultimately means that recalibration of NDIR meters which are designed to have a relatively large optical and thermal sensitivity and must meet very high demands and requirements concerning measurement technology will maintain these high qualities owing to the calibration under utilization of flowing test gases.

We claim:

1. In a calibration device provided for selective inclusion in radiation paths for purposes of calibrating a nondispersive infrared photometer which includes an infrared radiation source, possibly with modulation, a pair of chambers associated with measuring and reference paths, one of the chambers being a measuring chamber, a second one of the chambers being a reference chamber, said chambers being defined by a longitudinally divided tube and being symmetrically configured with respect to a longitudinal dividing and partitioning plane, the photometer, further including receiver, detector and filter structure, the calibration device comprising:

a carrier made of good heat conductive material and being provided with a first pair of calibration chambers and a second pair of calibration chambers so that in dependence upon the position of the carrier the first pair of calibration chambers or the second pair of calibration chambers is in optical alignment with the detector and with said measuring and reference chambers;

said carrier being movable in a direction that is in an interface plane defining respective partitioning of the pairs of calibration chambers and of the partitioning plane of the tube;

all calibration chambers being of similar cross section;

the first pair of these calibration chambers in the carrier including a gas filling that is the same in both calibration chambers while as to the second pair, one of the calibration chambers of the second pair contains the same kind of reference gas as contained in said reference chamber while the other calibration chamber is filled with a calibration gas; and window means associated with said calibration chamber pairs such that the number of optically effective boundary surfaces of the windows are the same regardless whether the first or the second pair are placed into alignment with said measuring and reference chambers.

2. Calibration device as in claim 1, wherein effective apertures of said calibration chambers of the first and second pair are slightly larger than effective apertures of the chambers of measuring and reference chambers.

3. Calibration device as in claim 1, wherein all the calibration chambers have semicircular cross section.

4. Calibration device as in claim 1, wherein said device is movable transverse to an optical axis of the measuring and reference chambers.

5. Calibration device as in claim 1, wherein said carrier is positioned to provide an intimate heat conductive relationship and transmission path for heat between the measuring and reference chamber on one hand and the detector system on the other hand.

* * * * *